United States Patent
Redel

(10) Patent No.: US 10,420,478 B2
(45) Date of Patent: Sep. 24, 2019

(54) X-RAY RECORDING WITH SUPERIMPOSED PLANNING INFORMATION

(71) Applicant: Thomas Redel, Poxdorf (DE)

(72) Inventor: Thomas Redel, Poxdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 100 days.

(21) Appl. No.: 15/684,609

(22) Filed: Aug. 23, 2017

(65) Prior Publication Data
US 2018/0055379 A1    Mar. 1, 2018

(30) Foreign Application Priority Data
Aug. 25, 2016  (DE) ................. 10 2016 215 966

(51) Int. Cl.
*A61B 5/026*   (2006.01)
*A61B 6/03*    (2006.01)
*A61B 8/08*    (2006.01)
*A61B 6/00*    (2006.01)
(Continued)

(52) U.S. Cl.
CPC ............. *A61B 5/026* (2013.01); *A61B 6/12* (2013.01); *A61B 6/463* (2013.01); *A61B 6/487* (2013.01); *A61B 6/504* (2013.01); *A61B 6/5217* (2013.01); *A61B 6/5235* (2013.01); *A61B 8/5238* (2013.01); *A61B 5/02007* (2013.01);
(Continued)

(58) Field of Classification Search
CPC ..................................................... A61B 5/026
USPC ....................................................... 345/629
See application file for complete search history.

(56) References Cited

U.S. PATENT DOCUMENTS 9,349,178 B1 *   5/2016   Itu .......................... G16H 50/50
2007/0135707 A1 * 6/2007   Redel ...................... A61B 6/481
                                                              600/424
(Continued)

FOREIGN PATENT DOCUMENTS

DE       102009004347 A1    6/2010

OTHER PUBLICATIONS

"Model Analysis of Red Blood Cell Flow Through Diverging and Converging Microvascular Bifurcations" 1994, Amini J.*
(Continued)

*Primary Examiner* — Javid A Amini
(74) *Attorney, Agent, or Firm* — Lempia Summerfield Katz LLC

(57) ABSTRACT

A method for operating an x-ray device, (e.g., a fluoroscope), is described herein. The method includes: creating planning information for a therapeutic intervention into a body vessel segment based on a reconstruction of the body vessel segment; providing the planning information to a processing unit of the x-ray device; providing the reconstruction of the body vessel segment to the processing unit; creating a recording of the body vessel segment introduced into a recording region of the x-ray device; registering the reconstruction of the body vessel segment with the body vessel segment in the recording region of the x-ray device; displaying the recording of the body vessel segment on a display device of the x-ray device; and superimposing a graphical representation of the planning information on the recording displayed on the display device, in order to increase the efficiency of the therapeutic intervention into the body vessel segment.

19 Claims, 2 Drawing Sheets

(51) Int. Cl.
*A61B 6/12* (2006.01)
*A61B 5/02* (2006.01)

(52) U.S. Cl.
CPC ............ *A61B 6/032* (2013.01); *A61B 6/503* (2013.01); *A61B 2576/00* (2013.01); *G06T 2207/30104* (2013.01)

(56) References Cited

U.S. PATENT DOCUMENTS

| | | | | |
|---|---|---|---|---|
| 2007/0247454 | A1* | 10/2007 | Rahn | A61B 6/032 345/419 |
| 2015/0302139 | A1* | 10/2015 | Sankaran | A61B 5/7275 703/20 |
| 2015/0339847 | A1* | 11/2015 | Benishti | G16H 50/30 382/131 |
| 2015/0342551 | A1* | 12/2015 | Lavi | G16H 50/30 600/431 |
| 2018/0365838 | A1* | 12/2018 | Lorenz | G06T 7/149 |

OTHER PUBLICATIONS

Efficient 3D Reconstruction of Vessels from Multi-views of X-Ray Angiography, 2013 13th International Conference on Computer-Aided Design and Computer Graphics.*

Reconstruction of Coronary Arteries from X-ray Angiography: A Review; Serkan C imena Ali Gooyaa, Michael Grassb, Alejandro F . Frangia, Epub Mar. 11, 2016.*

German Office Action for German Application No. 102016215966.6 dated May 12, 2017.

Morris, Paul D., et al. ""Virtual" (computed) fractional flow reserve: current challenges and limitations." JACC: Cardiovascular Interventions 8.8 (2015): 1009-1017.

Taylor, Charles A., Timothy A. Fonte, and James K. Min. "Computational fluid dynamics applied to cardiac computed tomography for noninvasive quantification of fractional flow reserve." Journal of the American College of Cardiology 61.22 (2013): 2233-2241.

* cited by examiner

X-RAY RECORDING WITH SUPERIMPOSED PLANNING INFORMATION

The application claims the benefit of German Patent Application No. DE 10 2016 215 966.6, filed Aug. 25, 2016, which is hereby incorporated by reference in its entirety.

TECHNICAL FIELD

The disclosure relates to a method for operating an x-ray device, (e.g., a fluoroscope). The disclosure also relates to a medical examination system with an x-ray device, which has a recording region into which a body vessel segment is able to be brought for creating a recording of the body vessel segment, and a display device for displaying the recording of the body vessel segment.

BACKGROUND

An established clinical characteristic variable is the Fractional Flow Reserve (FFR), which may be measured with a pressure wire, for example. In such cases, the pressure wire is guided past a stenosis in the body vessel or body vessel segment and determines the pressure there distal to the stenosis. This distal pressure is divided by the proximal pressure in order to calculate the fractional flow reserve.

It is possible, by a three-dimensional model of the body vessel segment or body vessel section in which the stenosis is contained, and further boundary conditions, (e.g., the blood flow in milliliters per second through the body vessel segment), to calculate the pressure curve via the stenosis by mathematical methods of fluid dynamics (e.g., computational fluid dynamics) and to compute a virtual value for the fractional flow reserve, a virtual FFR value, virtually on the basis of the three-dimensional model. Methods of this type are known and are described for example in the article by Paul D. Morris et al., "Virtual" (Computed) Fractional Flow Reserve—Current Challenges and Limitations," in JACC: Cardiovascular Interventions, Vol. 8, No. 8, 2015, pages 1009 to 1117, or the article by Charles A. Taylor et al., "Computational fluid dynamics applied to cardiac computed tomography for noninvasive quantification of fractional flow reserve," in: Journal of the American College of Cardiology, Vol. 61, No. 22, 2013, pages 2233 to 2241. Other methods of computation for a virtual FFR value are also known.

The approaches to virtual computation of the fractional flow reserve may be divided up into two groups: (1) non-invasive methods, in which geometry information about the body vessel segment or body vessel is obtained by computed tomography (CT), magnetic resonance tomography, or other methods; and (2) minimally-invasive methods, in which the geometry information is obtained in the cardiac catheter laboratory by an injection of contrast medium into the vessel with a subsequent x-ray recording. As a rule, a non-invasive examination of a patient is initially undertaken by computed tomography. As well as the diagnostic information about one or more vessel cross sections of the examined body vessel segment or body vessel, a virtual value for the fractional flow reserve may also be computed in such cases, which will be referred to below as the CT FFR value. By contrast, a virtual value for a fractional flow reserve, which is established by an angiography in the cardiac catheter laboratory, for example, will be referred to below as an angio FFR value.

The CT FFR method, (e.g., the computation of the virtual FFR value by a CT), has the advantage in this case that a three-dimensional model of the entire vascular tree, in which the body vessel or the body vessel segment with the stenosis is located, is available. It also allows a good determination of the perfused myocardial mass as well as of the perfusion flow derived from the proportion of the perfused myocardial mass. Furthermore additional information, such as a composition of the stenosis or of the plaque, may be established. The disadvantage in this case is the comparatively low spatial resolution and thus an imprecise geometry representation of the stenosis geometry.

By comparison with this method, the angio FFR method, e.g., the computation of a virtual FFR value using an angiography, has the advantage of a good spatial resolution, which makes a precise representation of the stenosis geometry possible. A disadvantage in this case is the estimation of the blood flow via the vessel cross sections. Here, even small errors may have large effects. The estimation of the blood flow via contrast media dynamics is complex and difficult in the angio FFR method. A further disadvantage is that the angio FFR method does not deliver any information about a state of the myocardial mass, which is important, for example, for recognizing any possible prior damage and enabling it to be considered during a treatment. Above and beyond this, geometry information of the vascular tree as a whole may only be obtained with great difficulty, which may be attributable to the relatively small detectors used in angiographies.

Also based on the results of the CT FFR method, the doctor may be presented with a suggested therapy. For this purpose, based on available information such as a computed tomography, a three-dimensional reconstruction derived from the computed tomography or models reduced or configured in another way, one or more different virtual treatments are carried out, and their success or possible influence is assessed on the basis of a newly calculated virtual FFR value or another clinical characteristic variable. At the end of such a process, planning information is then available about the treatment to be carried out, meaning the therapeutic intervention. The planning information in this case relates to the treatment method, for example, to a stent to be implanted, in the form of dimensions of the stent or a model of the stent, and/or a balloon dilatation and/or other measures, as well as to the treatment location in the body vessel or body vessel segment in the form of a precise localization and alignment as well as the value of the clinical characteristic variable, (e.g., the FFR value), to be achieved in accordance with the treatment.

SUMMARY AND DESCRIPTION

The scope of the present disclosure is defined solely by the appended claims and is not affected to any degree by the statements within this description. The present embodiments may obviate one or more of the drawbacks or limitations in the related art.

The underlying object of the disclosure is to increase the efficiency of a therapeutic intervention into a body vessel segment or a treatment of a body vessel segment.

The disclosure relates to a method for operating an x-ray device, (e.g., a fluoroscope or fluoroscopy x-ray device), with a series of acts. A first act is the creation of planning information for a therapeutic intervention into a body vessel segment or for a treatment of the body vessel segment, for example, in a section or of a section of a coronary vessel with a stenosis, based on a reconstruction of the body vessel segment. The body vessel segment may involve a diseased body vessel segment, which has a stenosis, for example. The body vessel segment may involve a segment of a coronary vessel. The reconstruction may involve a three-dimensional reconstruction. In one embodiment, the reconstruction is provided by a computed tomograph or is provided using data of a computed tomograph. As a further act, this is followed by provision of the planning information to a processing unit of the x-ray device as well as provision of the reconstruction of the body vessel segment to the processing unit.

This may be followed by bringing the body vessel segment or the patient with the body vessel segment respectively into a recording region of the x-ray device. This is followed by a creation of a recording, (e.g., of a fluoroscopy), of the body vessel segment brought into the recording region of the x-ray device, by the x-ray device. A further act is a registration of the reconstruction of the body vessel segment with the body vessel segment in the recording region of the x-ray device. In particular, the reconstruction may be registered with the created recording or fluoroscopy or, if a recording or a fluoroscopy has not yet been created, may be registered with a position of the patient and thus of the body vessel segment in the x-ray device, for example, with a patient table of the x-ray device.

The registration is to be understood here in the sense of an image registration, in which the reconstruction is placed in a defined, uniquely-determined spatial relationship with the x-ray device or with the body vessel segment, in order to bring the body vessel segment in the reconstruction into a spatial match with the body vessel segment in the recording or in the recording region of the x-ray device. Through the establishment, a spatial relationship of the medical device and the reconstruction stored in the device to the body vessel segment brought into the recording region is thus established.

There now follows a display of the recording or of the fluoroscopy of the body vessel segment on a display device of the x-ray device and a superimposition on the body vessel segment of the displayed recording or fluoroscopy with a graphical representation of the planning information. Because the reconstruction is registered with the body vessel segment in the recording region or with the recording region, the graphical representation may be superimposed here to match the location of the displayed recording precisely. Thus, for example, at the position of the body vessel segment at which a stent is to be implanted, a virtual stent may be superimposed on the recording. In one example, the recording or fluoroscopy involves an angiographic recording or angiographic fluoroscopy. In particular, the creation of the recording, the display of the recording, and the superimposition of a graphical representation of the planning information on the display may be effected as an ongoing process.

This has the advantage that the efficiency of the therapeutic intervention is increased, because an operator such as a doctor has a direct comparison of the current situation represented by the recording or fluoroscopy with the planned situation in front of them and is supported better than previously in carrying out the intervention. This is achieved in an efficient way, because the planning information may have been created by default at a preceding stage of a clinical procedure and this will be used multiple times, namely on the one hand, in the conventional workflow, and on the other hand, as is described here, may also continue to be used directly during the therapeutic intervention or the treatment. Above and beyond this, an improved quality, in particular an improved FFR computation in the cardiac catheter laboratory and savings in radiation dose and contrast medium may be achieved. Also, the intervention may be planned more precisely in this way, or the planning may be communicated to the operator more precisely.

In a further advantageous form of embodiment, there is provision for the planning information to include geometrical information about an implant to be introduced into the body vessel segment within the framework of the therapeutic intervention and/or physiological information about the body vessel segment and/or geometrical information about the body vessel segment. The geometrical Information about the body vessel segment may include a virtual representation of the vessel itself, for example, which, for better recognizability, is again superimposed on the recording. The physiological information about the body vessel segment may include a clinical characteristic variable, e.g., a value for a fractional flow reserve of the body vessel. The geometrical information about the implant may include a length of the implant and/or a diameter of the implant and/or a shape of the implant and/or spatial information about a desired position, (e.g., a desired final position), of the implant to be implanted into the body vessel segment within the framework of the therapeutic intervention, in particular a position of the implant in the body vessel and/or an orientation of the implant relative to the body vessel. This has the advantage that the therapeutic intervention will be well visualized in its course and in its destination to be reached, and thus it is made possible to carry out the treatment or the therapeutic intervention in an efficient manner.

In one example, the implant may be a stent, e.g., a so-called endoluminal vessel prosthesis, and/or a balloon element for a balloon dilation. The "and" may be to be understood in particular here in the sense of "one after the other," whereby the implant initially includes a balloon element for a balloon dilation and thereafter a stent, which is to be implanted permanently in the body vessel segment. It is precisely for the implants that a monitoring of the intervention as well as a correction of the planning data made possible by the described method is particularly useful, because it is critical for a successful treatment.

In a further advantageous form of embodiment, there may be provision for the superimposed graphical representation of the planning information to be configured to a movement of the body vessel segment. In particular, the superimposed graphical representation may be configured to a breathing movement, e.g., a displacement of the body vessel for example, and/or to a pulse movement, e.g., a deformation such as a widening for example. When a four-dimensional reconstruction, (e.g., a reconstruction with three spatial dimensions and one-time dimension), is used and a correspondingly four-dimensional, e.g., time-dependent computation of a value of the clinical characteristic variable, (e.g., of the FFR values), the superimposition may thus be undertaken synchronized with a heart phase. This has the advantage that the planning information and the recording are especially well tuned to one another, so that the accuracy and thus the efficiency of the therapeutic intervention will be increased.

In a further advantageous form of embodiment, there is provision for a recording angle of the recording or fluoroscopy to be predetermined as a function of the reconstruction, which is registered with the body vessel segment arranged in the recording region, for example, via a registration of the reconstruction with the patient table. The recording angle may be predetermined in this case such that the recording angle is essentially perpendicular, (e.g., perpendicular+/−a predetermined tolerance, which for example may amount to 5, 10 or 15 degrees), to a main extent direction or a long axis of the body vessel segment. The main extent direction of the body vessel segment may involve a main extent direction of the body vessel segment in the region of a stenosis. The main extent direction of the body vessel segment in this case may correspond to a long axis of the implant, in particular, to a long axis of a stent. This has the advantage that the information contained in the reconstruction will be used to optimize the recording or the recording angle, because in this way the body vessel segment may be seen well, in particular, without a geometrical shortening, on the recording.

In a further embodiment, there is provision for an operator, (e.g., a doctor), to be given an opportunity during the superimposition to adapt the planning information manually. In particular, this may be effected by a touch-sensitive display element of the display device, which displays the recording or fluoroscopy and the graphical representation of the planning information. This may be realized, for example, with a touchscreen or with other non-contact interaction concepts. This has the advantage that the flexibility and thus the efficiency of the method are increased. It is because preliminary information, on which the reconstruction of the body vessel segment may be based, is less precise than a recording made later during the therapeutic intervention that new information may be produced in the further course of the treatment or therapy, which, in the described form of embodiment, may efficiently be considered by the operator.

In a further advantageous form of embodiment, there may be provision for a clinical characteristic variable of the body vessel segment to be established before the superimposition, using the created recording or fluoroscopy and the planning information, of which the graphical representation is to be superimposed on the recording, to be updated as a function of the established clinical characteristic variable, and then for the graphical representation of the updated planning information to be superimposed on the displayed recording or fluoroscopy. This has the advantage that the displayed planning information is up-to-date. Also, in this way, the planning information is adapted in a verifiable, quantifiable way to the current situation, which is represented by the created recording and takes account of the current situation.

In this case, there may be provision for the planning information only to be updated if a check on the planning information based on the established clinical characteristic variable delivers a negative checking result. A negative checking result may be present if conflicts or differences arise between the situation represented by the reconstruction and that represented by the recording. For example, the checking may be realized by the clinical characteristic variable being established as a supplementary value using the reconstruction and the characteristic variable established using the reconstruction being compared with the clinical characteristic variable established using the recording or fluoroscopy. A negative checking result may then be present, for example, if the clinical characteristic variable established using the recording deviates from the characteristic variable established using the reconstruction by more than a predetermined amount.

This has the advantage that in this way possible errors or inaccuracies may be prevented, but at the same time smaller deviations, which are naturally likely to occur in the clinical environment, do not lead to an expensive and possibly unnecessary adaptation of the planning information and thus of the therapeutic intervention.

In an advantageous manner, there may be provision in this case for the clinical characteristic variable to be established using the reconstruction of the body vessel segment using reconstruction data on which the reconstruction of the body vessel segment is based. The fact that the clinical variable may thus be established both using the reconstruction and also using the recording enables this to be computed in an especially precise way.

For example, in this way the CT FFR method and angio FFR method mentioned at the start may be combined. This may be effected by initially, before the therapeutic intervention and thus before the creation of the recording of the body vessel segment, a computed tomography, (e.g., an angiographic computed tomography of the body vessel segment), being created and a corresponding value, (e.g., a CT FFR value), being computed for the body vessel segment. In this act, as well as the CT FFR value, a plurality of further results occur, (e.g., segmentation information of the body vessel), of which the body vessel segment is part, including corresponding mid or center lines, a value for a myocardial mass and/or for a myocardial volume, from which in their turn further parameters such as the blood flow, the myocardial resistance or other values may be derived, which are necessary for an estimation of the CT FFR value. In addition, information is available about the body vessel as a whole, for example, in the form of a vascular tree. The information may be available, for example, as three-dimensional information, but also as a reduced model with only the information relevant to the flow. In this case, the reconstruction of the computation of the clinical characteristic variable, here of the CT FFR value, lies in the restricted spatial resolution of the computed tomography by comparison with a two or three-dimensional angiography of the body vessel segment, as is achieved for example in the cardiac catheter laboratory. Thus, the combined establishment of the clinical characteristic variable using both the reconstruction of the body vessel segment, for example, from the computed tomograph, and also using the created recording is a method of calculation for the characteristic variable. By establishing the clinical characteristic variable using the previously known reconstruction of the body vessel segment, current information from the recording may now be combined with previously available information from the reconstruction for establishing the current value of the clinical characteristic variable.

The clinical characteristic variable of the body vessel segment may be established, for example, by a first provision of a three-dimensional reconstruction of the body vessel with the body vessel segment and a second provision of a segmented recording of the body vessel segment followed by a first extraction of at least one global feature of the body vessel, which relates to a vascular tree, from the three-dimensional reconstruction and a second extraction of at least one local feature of the body vessel segment, which relates to a body vessel stem, from the recording, which is followed by an establishment of the clinical variable for the body vessel segment as a function of the extracted local and global feature.

For a computation of the clinical characteristic variable, for example, of the CT FFR value, geometrical models and mappings from the image information of the reconstruction are computed or estimated. After the registration of the reconstruction with the recording region or with the recording has taken place, the information from the reconstruction of the body vessel segment may be combined at least locally with the recording or fluoroscopy and thus a more precise value for the clinical characteristic variable, for example, for the angio FFR value, may be computed. Thus, for example, a three-dimensional vascular tree or a three-dimensional reconstruction of the body vessel from the computed tomography, which is available after a preliminary computation of the clinical characteristic variable, in the present case of the CT FFR value, for example, may be used as a three-dimensional model, and may be supplemented by the more precise three-dimensional information from the fluoroscopy, (e.g., the coronary angiography), or may be combined with the information. Here, a global course of the vascular tree or body vessel as a lower-dimensional description, (e.g., as a resistance network from the reconstruction), may be used. The lower-dimensional description may be combined at respective inflow and outflow points of the global course of the vessels with information from the more precise recording or fluoroscopy. In a further possibility, values known from the reconstruction of the body vessel segment, such as a blood flow, may be used for a boundary condition for establishing the clinical characteristic variable and may be linked with information from the recording and the reconstruction. This enables an even more precise computation of the clinical characteristic variable to be carried out.

This new, combined computed value for the clinical variable may now serve as a basis for a new therapy planning or new planning information or a planning update.

In a further form of embodiment, there is provision in this case for the clinical characteristic variable to include a hemodynamic characteristic variable, in particular, a value of a fractional flow reserve of the body vessel segment and/or an instantaneous pressure ratio for the body vessel segment and/or an instantaneous wave-free pressure ratio for the body vessel segment (e.g., instantaneous wave-free ratio, iFR) and/or a pressure ratio between a distal pressure and an aortic pressure for the body vessel segment and/or a blood flow through the body vessel segment and/or a blood pressure in the body vessel segment and/or a wall shear force in the body vessel. The clinical characteristic variables are dependent to a particular extent on the small deviations in the data from which they are derived, so that here an updating of the planning information is especially advantageous.

The disclosure also relates to a medical examination system with an x-ray device, (e.g., with a fluoroscope), which is able to be introduced into a recording region, in which a body vessel segment for creating a recording or fluoroscopy of the body vessel segment is located, and has a display device for displaying the recording or fluoroscopy of the body vessel segment. Furthermore, the medical examination system also has a medical imaging device for provision of a reconstruction of the body vessel segment to a processing unit of the x-ray device. The medical imaging device may involve a computed tomograph or the medical imaging device may include a computed tomograph. The processing unit of the x-ray device is able to be coupled to the medical imaging device and is designed to register the reconstruction of the body vessel provided with the body vessel segment in the recording region of the x-ray device. The display device of the x-ray device is designed in this case to superimpose a graphical representation of planning information provided to the processing unit for a therapeutic intervention displayed for a recording or fluoroscopy on the body vessel segment, wherein the planning information is created on the basis of the reconstruction of the body vessel segment.

Advantages and advantageous forms of embodiment of the medical examination system correspond here to advantages and advantageous forms of embodiment of the described method.

The features and combinations of features given here in the description, as well as the features and combinations of features given below in the description of the figures and/or shown solely in the figures are not only able to be used in the combination specified in each case, but also in other combinations or on their own, without departing from the framework of the disclosure. Thus, versions of the disclosure that are not shown and explained explicitly in the figures, but which originate and are able to be created through separated combinations of features from the explained versions, are to be seen as included and disclosed. Thus, versions and feature combinations that thus do not have all features or an originally formulated dependent or independent claim are to be seen as disclosed. Above and beyond this embodiments and combinations of features that go beyond or deviate from the combination of features set out in the dependent claims of the claims, in particular, through the information given above, are to be seen as disclosed.

BRIEF DESCRIPTION OF THE DRAWINGS

Exemplary embodiments will be explained in greater detail below on the basis of schematic drawings. In the figures.

In the figures, identical elements or elements with an identical function are provided with the same reference characters.

DETAILED DESCRIPTION

Figure 1:
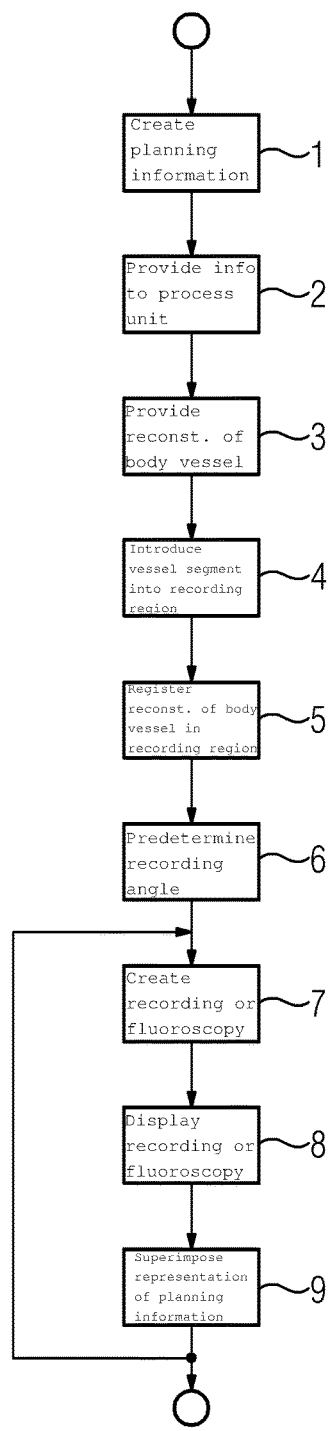
FIG. 1 depicts a schematic flow diagram of a first form of embodiment of a method for operating an x-ray device.

FIG. 1 depicts a schematic flow diagram of a form of embodiment of a method for operating an x-ray device. A first act is a creation 1 of planning information for a therapeutic intervention into a body vessel segment, which in the present example has a stenosis. The therapeutic intervention, in the example shown, involves an implantation of a stent in a coronary vessel as body vessel segment. The planning information is created in the present example on the basis of a here three-dimensional reconstruction of the body vessel segment, which, in the example shown, originates from a computed tomograph.

The idea may thus be seen as also using the information from a computed tomograph in a cardiac catheter laboratory in the present example and registering the pre-interventional computed tomography with the position of the patient on the heart catheter table and furthermore superimposing the planning information of the therapy or the treatment in this example in the cardiac catheter laboratory within the framework of a fluoroscopy on a life monitor for example with a recording or fluoroscopy. For this, after the creation of the planning information before the intervention, e.g., prior to the intervention, there are still a series of further acts required.

Thus, in an additional act, there is the provision 2 of the planning information to a processing unit of the x-ray device designed in the present example as a fluoroscope. A provision 3 of the reconstruction of the body vessel segment to the processing unit is also undertaken here. Within the framework of the therapy or the treatment the patient and thus the body vessel segment will also be introduced into a recording region of the x-ray device, in order to create a recording, here a fluoroscopy, in the region.

Before a creation 7 of the recording by the x-ray device, there is also first of all a registration 5 of reconstruction of the body vessel segment with the body vessel segment in the recording region of the x-ray device beforehand. This is followed in the present form of embodiment by a predetermination 6 of a recording angle for the recording or fluoroscopy as a function of the reconstruction. In this case, the recording angle is predetermined such that it is essentially perpendicular to a main extent direction of the body vessel segment with the stenosis. In addition, further parameters may also be considered in the selection of the recording angle, thus, for example, a coverage or overlapping of the body vessel segment with the stenosis with further body vessel segments or other body vessels on the recording from the predetermined recording angle, as is to be expected as a result of the available and provided three-dimensional reconstruction.

Thus, through the planning, the knowledge about the location of the stenosis in the three-dimensional model is used to carry out the planning of the recording angle. Thus, the doctor may move directly, without additional recording and thus with less radiation and contrast medium for the patient, to the optimal angulation, in which the stenosis is shown without any shortening. Above and beyond this, there is the possibility of computing complete invasive diagnostics in the cardiac catheter laboratory with the associated angulations in advance. This is above all advantageous for patients who have an anatomy in the body vessel segment, (e.g., a coronary anatomy), which deviates from a standard anatomy.

In a next act, in the present example, there is a display 8 of the recording or of the fluoroscopy of the body vessel segment on a display device of the x-ray device. The creation 7 of the recording and the display 8 of the recording occurs continuously here, as may exist for a fluoroscopy. In a last act, there is now a superimposition 9 of a graphical representation of the planning information on the recording or fluoroscopy shown on the display device. Thus, the recording or the fluoroscopy image, (e.g., for a stent), which is to be inserted as an implant into the body vessel segment, may have a virtual stent, or for a balloon dilation, a virtual balloon shown superimposed on it. As a graphical representation of the corresponding planning information, a planned target restriction of the body vessel segment after the therapeutic intervention may also be displayed for example. Also, a display of the body vessel segment itself may be superimposed as a virtual body vessel segment on the recording. A further graphical representation of planning information is a spatially-resolved superimposition of a pressure curve along the body vessel segment, which may be shown color-coded for example. Also, the localization of the stenosis, e.g., the precise location of the stenosis, and/or virtual value of a fractional flow reserve may have the recording or fluoroscopy superimposed on it here, in the form of a coloration, for example. With this, an overview of the planning is improved and a radiation dose and contrast medium are saved. Above and beyond this the therapeutic intervention may be planned more precisely in this way and may be better configured to actual previously-found features reflected in the recording.

Figure 2:
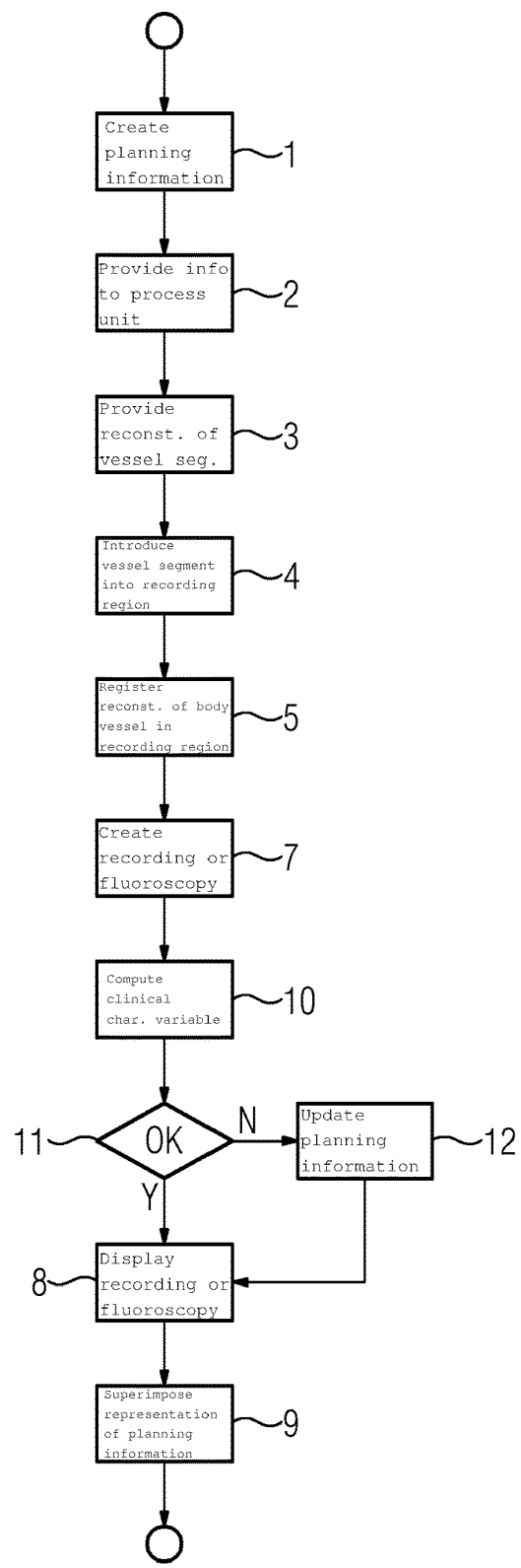
FIG. 2 depicts a flow diagram of a further form of embodiment of a method for operating an x-ray device.

FIG. 2 depicts a schematic flow diagram of a further form of embodiment of a method for operating an x-ray device. The features of the first embodiment variant in this case are able to be freely combined with the features of the embodiment variant described below and vice versa. As in the embodiment variant described above, there is first of all here a creation 1 of the planning information, a provision 2 of the planning information, a provision 3 of the reconstruction of the body vessel segment, an introduction 4 of the body vessel segment into the recording region of the x-ray device, a registration 5 of the reconstruction of the body vessel segment with the body vessel segment in the recording region of the x-ray device, and a creation 7 of a recording or fluoroscopy. This may relate, as in the exemplary embodiment described above, to a coronary vessel with a stenosis, in which a stent is to be implanted.

In the example shown, there is now a computation 10 of a clinical characteristic variable, which in the present example is defined as a virtual value of a fractional flow reserve of the body vessel segment with the stenosis. During the computation 10, in this case data from another computation of the medical characteristic value, in the present example of the virtual value for the fractional flow reserve, is considered, which has already been computed before the creation 7 of the recording. Thus, for example, information from an examination made previously within the framework of a computed tomography, on which in the present example the three-dimensional reconstruction of the body vessel segment is also based, is used. Information, which may be taken into account here for computation of the angio FFR value, here includes segmentation information of the body vessel segment or of a body vessel, of which the body vessel segment is a part, mid or center lines of the body vessel segment or of the body vessel, as well as a value for the myocardial mass or a myocardial volume, from which further parameters such as the blood flow, the myocardial resistance and other variables will be derived, which are required for an estimation of a virtual FFR value. Also, three-dimensional information about the body vessel as a whole, of which the body vessel segment is a part, may be provided. This may be effected, if necessary, as a reduced model with just the information that is relevant for a flow computation.

This preliminary information is now used to compute an especially precise value for the fraction flow reserve of the body vessel segment. For this, geometrical features or other boundary conditions from the three-dimensional reconstruction of the computed tomography after the registration 5 may be at least locally combined and then a more precise angio FFR value may be computed. For example, the three-dimensional vascular tree from the computed tomography, which is available in any event after the CT FFR computation as a three-dimensional reconstruction, may be used and supplemented by locally more precise three-dimensional information from the recording or fluoroscopy in the form of a coronary angiography or be combined with said information. For example, in this way a global vessel course in the body vessel may be used as a lower-dimensional description, for example, as a resistance network. In the inflow and outflow points of the course of the vessels the lower-dimensional description is combined with information from the more precise model, here, for example, the coronary angiography.

In a further variant, the values for boundary conditions already present, such as the blood flow in milliliters per second from the CT FFR method, (e.g., from the measurement of the myocardial mass), may be linked to the information from the two-dimensional recording or fluoroscopy and the three-dimensional reconstruction of the body vessel segment, in order to determine an even more precise value for the fractional flow reserve.

This combined computed value for the clinical variable, which is given here as a virtual value for the fractional flow reserve, now subsequently serves as a basis for an improved therapy planning or a planning update for the therapeutic intervention.

Thus, in an additional act, a check 11 is carried out as to whether the combined computed characteristic variable, e.g., here the combined computed angio FFR value, conflicts in any way with the originally created planning information. This may be established by a value of the clinical characteristic variable, which was originally used in the creation 1 of the planning information, being compared with the combined computed value of the clinical characteristic variable from the computation 10 and a display 8 and also there only being the superimposition 9 of a graphical representation of the planning information from the creation 1 on the displayed recording, if the original value of the clinical characteristic variable and the combined established value of the clinical characteristic variable deviate from one another by less than a predetermined amount.

If the check 11 delivers a negative checking result, such a deviation will thus be determined, so that, in the form of embodiment shown, an updating 12 of the planning information is carried out and then in act 9 this updated planning information has the recording superimposed on it, in order to make possible an updated therapy guidance and thus best-possible support of an operator during the therapeutic intervention.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating an x-ray device, the method comprising:
creating planning information for a therapeutic intervention into a body vessel segment based on a reconstruction of the body vessel segment, wherein the planning information comprises geometrical information about an implant to be introduced into the body vessel segment within a framework of the therapeutic intervention, physiological information about the body vessel segment, or a combination thereof;
providing the planning information to a processing unit of the x-ray device;
providing the reconstruction of the body vessel segment to the processing unit;
creating a recording of the body vessel segment introduced into a recording region of the x-ray device by the x-ray device;
registering the reconstruction of the body vessel segment with the body vessel segment in the recording region of the x-ray device;
displaying the recording of the body vessel segment on a display device of the x-ray device; and
superimposing a graphical representation of the planning information on the recording shown on the display device.

2. The method of claim 1, wherein the x-ray device is a fluoroscope.

3. The method of claim 1, wherein the planning information is the physiological information about the body vessel segment.

4. The method of claim 3, wherein the physiological information comprises a clinical characteristic variable.

5. The method of claim 4, wherein the clinical characteristic variable is a value for a fractional flow reserve of the body vessel.

6. The method of claim 1, wherein the superimposed graphical representation of the planning information is configured to a movement of the body vessel segment.

7. The method of claim 6, wherein the movement of the body vessel segment is a breathing movement, a pulse movement, or a combination thereof.

8. The method of claim 1, wherein a recording angle of the recording is predetermined as a function of the reconstruction.

9. The method of claim 8, wherein the recording angle is essentially perpendicular to a main extent direction of the body vessel segment.

10. The method of claim 1, wherein, during the superimposition, an operator is given an opportunity of adapting the planning information by a touch-sensitive display element of the display device, which displays the recording and the graphical representation of the planning information.

11. The method of claim 1, wherein, before the superimposition in accordance with the displaying, using the created recording, a clinical characteristic variable of the body vessel segment is established and the planning information is updated as a function of the established clinical characteristic variable, before the graphical representation of the updated planning information in accordance with the displaying is superimposed on the displayed recording.

12. The method of claim 11, wherein the clinical characteristic variable is established using the reconstruction of the body vessel segment.

13. The method of claim 11, wherein the clinical characteristic variable comprises a hemodynamic characteristic variable selected from the group consisting of: a value of a fractional flow reserve of the body vessel segment, an instantaneous pressure ratio for the body vessel segment, an instantaneous wave-free pressure ratio for the body vessel segment, a pressure ratio between a distal pressure and an aortic pressure for the body vessel segment, a blood flow through the body vessel segment, a blood pressure in the body vessel segment, a wall shear force in the body vessel segment, and combinations thereof.

14. A medical examination system comprising:
an x-ray device having a recording region, into which a body vessel segment is able to be introduced for creating a recording of the body vessel segment,
a display device configured to display the recording of the body vessel segment; and
a medical imaging device configured to provide a reconstruction of the body vessel segment to a processing unit of the x-ray device,
wherein the processing unit is configured to register the provided reconstruction of the body vessel with the body vessel segment in the recording region of the x-ray device, and
wherein the display device is configured to superimpose on the displayed recording a graphical representation of planning information provided for a therapeutic intervention into a body vessel segment, wherein the planning information is created based on the reconstruction of the body vessel segment, and wherein the planning information comprises geometrical information about an implant to be introduced into the body vessel segment within a framework of the therapeutic intervention, physiological information about the body vessel segment, or a combination thereof.

15. The method of claim 1, wherein the planning information is the geometrical information about an implant to be introduced into the body vessel segment within a framework of the therapeutic intervention.

16. The method of claim 15, wherein the geometrical information comprises a length of the implant, a diameter of the implant, a shape of the implant, spatial information about a desired location of the implant to be implanted into the body vessel segment within the framework of the therapeutic intervention, or a combination thereof.

17. The method of claim 16, wherein the spatial information is a position of the implant in the body vessel, an orientation of the implant relative to the body vessel, or a combination thereof.

18. The method of claim 16, wherein the desired location is a desired final location of the implant.

19. The method of claim 15, wherein the implant comprises a stent, a balloon element, or a combination thereof.

* * * * *